(12) United States Patent
McAteer et al.

(10) Patent No.: US 6,596,872 B2
(45) Date of Patent: Jul. 22, 2003

(54) PROCESS FOR PREPARING ALKENYL-SUBSTITUTED HETEROCYCLES

(75) Inventors: Colin H. McAteer, Indianapolis, IN (US); Aaron J. Edwards, Greenwood, IN (US); Yarlagadda V. Subba Rao, Indianapolis, IN (US)

(73) Assignee: Reilly Industries, Inc., Indianapolis, IN (US)

( * ) Notice: Subject to any disclaimer, the term of this patent is extended or adjusted under 35 U.S.C. 154(b) by 0 days.

(21) Appl. No.: 10/040,726

(22) Filed: Oct. 22, 2001

(65) Prior Publication Data

US 2002/0123633 A1 Sep. 5, 2002

Related U.S. Application Data

(60) Provisional application No. 60/242,174, filed on Oct. 20, 2000.

(51) Int. Cl.$^7$ .......................................... C07D 213/127
(52) U.S. Cl. ................... 546/252; 546/252; 546/253; 546/254
(58) Field of Search ................ 546/252, 253, 546/254

(56) References Cited

U.S. PATENT DOCUMENTS 6,008,364 A    12/1999   Yamamoto et al.

FOREIGN PATENT DOCUMENTS

JP           46-37592    * 11/1971

OTHER PUBLICATIONS

"Methylation of pyridine over zeolites", Kameswari et al., Studies in Surface Science and Catalysts, vol. 84 (1994) pp. 1959–1964.*

"Oxidative methylation of α–, β–, and γ–picolines with methane vinylpyridines and ethylpyridines over mono–and bialkali promoted magnesia catalysts", Ruckenstein and Reddy, *Catalysts Letters,* 29 (1994) pp. 217–224.

"Catalytic osydehydrogenation of 2–ethylpyridine", Moscotti and Forni, *Applied Catalysts,* A; General 134 (1996), pp. 263–274.

*Organic Conversions with Zeolites,* 49 Kashiwagi et al., 1982, pp. 49–51.

"Methylation of pyridine over zeolites", Janeswaru et al., *Studies in Surface Science and Catalysis,* vol. 84 (1994) pp. 1959–1964.

"Base catalyzed synthesis of vinylpyridines from picolines over basic modified zeolites", Kulkarni et al., *Industrial Applications of Zeolites Proceedings,* Oct. 22–25, 2000, Brugge, Belgium, pp. 117–127.

* cited by examiner

*Primary Examiner*—Alan L. Rotman
*Assistant Examiner*—Janet L Coppins
(74) *Attorney, Agent, or Firm*—Woodard, Emhardt, Moriarty, McNett & Henry LLP

(57) ABSTRACT

Described are preferred processes for preparing alkenyl-substituted nitrogenous heterocycles such as vinylpyridines, which comprise reacting a corresponding methyl-substituted heterocycle with a $C_1$ compound such as formadehyde in the vapor phase over a zeolite catalyst having acidic and basic catalytic sites. The preferred zeolite is a medium-pore zeolite, for example having a constraint index of about 0.5 to about 12. Processes of the invention can be conducted as facile, one-step syntheses utilizing relatively low ratios of alkyl-substituted starting heterocycle (e.g. α-picoline or γ-picoline) to formaldehyde while nonetheless achieving high selectivities and yields of the corresponding alkenyl compound.

22 Claims, No Drawings

PROCESS FOR PREPARING ALKENYL-SUBSTITUTED HETEROCYCLES

This application claims the benefit of Provisional Application No 60/242,174, filed Oct. 20, 2000.

BACKGROUND

The present invention relates generally to the production of alkenyl-substituted heterocyclic compounds, and in particular to processes for preparing vinyl-substituted heterocycles such as 2- or 4-vinylpyridines by reaction of corresponding picolines and formaldehyde in the vapor phase over a solid catalyst.

As further background, alkenyl-substituted heterocyclic compounds such as 2- and 4-vinylpyridine are useful in the preparation of polymers which enjoy a wide variety of applications, including for example fabric stiffeners for the production of biased-ply car tires, in the preparation of ion exchange resins, in dye transfer inhibition, and in the research and medical fields generally. With the goal of developing facile syntheses, a few one-step routes to vinylpyridines have been proposed.

For instance, Bonnemann et al., have proposed a reaction of two moles of acetylene with acrylonitrile using a soluble $[(\eta^6\text{-}1\text{-}PhC_5H_5)Co(1,5\text{-cyclooctadiene})]$. *Applied Homogeneous Catalysis with Organometallic Compounds,* Cornils, B., Herrmann, W. A., Eds.; VCH: Weinheim, Germany, 1996, Volume 2, pp. 1106–1107.

A few reports also propose a one-step vapor-phase production of vinylpyridine over a solid catalyst. More recently, the oxidative dehydrogenation of 2-ethylpyridine to 2-vinylpyridine over $SnO_2/SiO_2$ (Moscotti et al., *Applied Catalysis* 1996, 134, 263–274) or molybdenum-based catalysts (Belomestnykh et al., *Chemistry of Heterocyclic Compounds,* 1994, 30, 701–708) have been proposed. Others have suggested the oxidative coupling of $CH_4$ with α-, β-, and γ-picoline to give the corresponding vinylpyridine over Na—Cs/MgO (Ruckenstein, et al., *Catalysis Letters,* 1994, 29, 217–224). Watanabe et al., in an earlier report proposed the use of $H_3PO_4/SiO_2$, and $ZnX_2/SiO_2$ (X=Cl, F) to produce 2- and 4-vinylpyridine from picoline/formaldehyde feeds.

In light of this background, there remains a need for an improved process for preparing alkenyl-substituted heterocycles such as 2- and 4-vinylpyridines. The present invention addresses this need.

SUMMARY OF THE INVENTION

It has been discovered that alkenyl-substituted heterocycles can be prepared effectively by the reaction of formaldehyde with a corresponding alkyl-substituted heterocycle in the vapor phase in the presence of a zeolite catalyst, wherein the catalyst contains both acidic and basic catalytic sites. Accordingly, in one preferred aspect, the present invention provides a process for preparing a vinyl-substituted nitrogenous heterocycle, comprising reacting a methyl-substituted nitrogenous heterocycle with formaldehyde in the vapor phase in the presence of a zeolite catalyst modified with at least one metal cation that provides basic catalytic sites, so as to form a corresponding vinyl-substituted nitrogenous heterocycle. In a most preferred form, this process involves reacting an α-picoline or γ-picoline with formaldehyde in the presence of a medium pore zeolite catalyst modified with at least one metal cation so as to form a corresponding 2-vinylpyridine or 4-vinylpyridine compound. The metal cation is preferably an alkali metal cation, more preferably selected from the group consisting of sodium, potassium, rubidium and cesium. Processes of the invention are effectively carried out at temperatures in the range of about 250° C. to about 500° C., more preferably about 350° C. to about 450° C. Advantageous processes are carried out with a relatively low ratio of picoline (or other starting heterocycles) to formaldehyde, for example less than about a 5:1 molar ratio, more preferably less than about a 5:1 molar ratio, more preferably less than about a 3:1 molar ratio. Most preferred processes are conducted with a starting heterocycle (e.g. picoline) to formaldehyde molar ratio of about 1:1 or less. Desirably, the zeolite employed has a constraint index of about 0.5 to about 12, and can be a phosphorous-stabilized zeolite.

The present invention provides novel processes for preparing vinyl-substituted heterocycles which can be conducted in the vapor phase as one-step reactions while providing high yields and selectivities and not requiring the use of high picoline-to-formaldehyde ratios. Additional objects and advantages of the invention will be apparent from the descriptions herein.

DESCRIPTION OF THE PREFERRED EMBODIMENT

For the purposes of promoting an understanding of the principles of the invention, reference will now be made to the certain embodiments thereof and specific language will be used to describe the same. It will nevertheless be understood that no limitation of the scope of the invention is thereby intended, such alterations, further modifications and applications of the principles of the invention as described herein being contemplated as would normally occur to one skilled in the art to which the invention relates.

As disclosed above, the present invention provides novel processes for the production of alkenyl-substituted heterocycles, for example vinyl-substituted heterocycles. The inventive processes are conducted in the vapor phase over zeolite catalysts. Processes of the invention involve the reaction of an appropriate alkyl-substituted nitrogenous heterocycle with formaldehyde at an elevated temperature, to yield a corresponding alkenyl-substituted nitrogenous heterocycle. More preferred processes of the invention include the reaction of α-picoline or γ-picoline under such conditions to provide the corresponding 2-vinylpyridine or 4-vinylpyridine compound.

Turning now to a more detailed discussion of the starting materials for processes of the invention, the alkyl-substituted heterocycle is generally an aromatic heterocyclic compound containing one or more nitrogens in the ring, preferably a single nitrogen in the ring. The aromatic ring will typically contain from about 4 to about 6 members.

Particularly preferred starting compounds are pyridines and pyrazines containing an alkyl group (e.g. a $C_1$ to $C_5$ alkyl group, especially methyl, ethyl or propyl) on an activated position of the ring, for example the 2- or 4-position of a pyridine ring as in α-picoline, γ-picoline, or the 2-position of a pyrazine ring as in 2-methylpyrazine. The heterocycle may also have a substituent on one or more non-reactive positions of the heterocyclic ring which will not be altered under the conditions of the reaction, for example on the 3-position and/or 5-position of a pyridine ring. Such substituent may be, for example, a $C_1$ to $C_5$ hydrocarbon group such as an alkyl group. Suitable starting materials for the present invention thus also include 2,3-dialkypyridines, for example 2,3-dimethylpyridine and 2-ethyl-3-methylpyridine which may be reacted with formaldehyde to form 2-vinyl-3-methylpyridine and 2-propenyl-3-methylpyridine, respectively; 2,5-dialkypyridines, for example 2,5-dimethylpyridine and 2-ethyl-5-methylpyridine which may be reacted with formaldehyde to form 2-vinyl-5-methylpyridine and 2-propenyl-5-methylpyridine, respectively; and 2,3,5-trialkylpyridines, for instance 2,3,5-trimethylpyridine and 2-ethyl-3,5-dimethylpyridine which can be reacted with formaldehyde to form 2-vinyl-3,5-dimethylpyridine and 2-propenyl-3,5-dimethylpyridine, respectively.

The alkyl-substituted heterocycle will be reacted with a compound containing a single carbon, preferably formaldehyde. In this regard, the formaldehyde in the reaction zone can be provided by feeding formaldehyde itself to the reaction zone, or compounds which form formaldehyde under the conditions of the reaction. For example, the formaldehyde feed may take the form of an aqueous solution of formaldehyde, preferably a concentrated solution. Illustratively, an aqueous solution containing twenty weight percent or more formaldehyde, preferably thirty weight percent or more formaldehyde, can be used. Alternatively, the formaldehyde feed may take the form of trioxane, which essentially provides the equivalent of three formaldehyde molecules to the reaction zone.

Processes of the invention will employ a zeolite catalyst modified to contain both acidic and basic catalytic sites. In this regard, zeolites are known to contain native acidic ($H^+$) sites. In accordance with the invention, the zeolite will be modified with an appropriate metal cation to provide basic catalytic sites as well. Suitable metal cations will be known to those skilled in the art, but preferably the metal cation is an alkali metal cation or an alkaline-earth metal cation, and most preferably an alkali metal cation such as sodium, potassium, rubidium or cesium. Additional metal cations such as thallium can be used, and illustrative candidates are disclosed in the specific Examples below.

Modification of the zeolites to incorporate the metal cation can be conducted in conventional fashion, including for example impregnation of the zeolite powder with a solution of an appropriate metal salt followed by drying and calcination, ion exchange into the zeolite powder followed by similar processing or the like. Similarly, the metal cation-loading can take place either before or after the zeolite is bound with a suitable carrier. Typically, the zeolite catalyst will be modified to contain about 1% to about 20% by weight of the metal cation (excluding consideration of any binder present), more typically in the range of about 1% to about 10% by weight.

Preferred zeolite catalysts for use in the invention will have a medium-pore structure. For example, the zeolite catalyst preferably has a constraint index of about 0.5 to about 12, including e.g. zeolite MFI and zeolite beta (BEA). More preferred zeolite catalysts will have a constraint index of about 4 to about 10, with a preferred zeolite catalyst being MFI, having a constraint index of about 8.3. In this regard, this "constraint index" is a conventional term which is well-known and used in the art to characterize porous catalyst materials including zeolites, and as used herein refers to the value as determined in the conventional fashion which is described for example in Frillette et al, *Journal of Catalysis*, 67, 218–222 (1981). Advantageous processes of the invention can be carried out using phosphorous-stabilized zeolite catalysts, such as phosphorous-stabilized MFI or phosphorous-stabilized BEA.

The zeolite catalyst will typically be used in bound form with a suitable carrier such as silica, alumina, silica-alumina, or a clay.

As to conditions of the reaction, processes of the invention will typically take place at a temperature of about 200° C. to about 500° C., more preferably about 350° C. to about 450° C. The reactions will take place in the vapor phase, preferably conducted continuously by the passage of the reactants into and through a vapor-phase reactor containing the zeolite catalyst. The reactants can be vaporized and combined prior to contacting the zeolite catalyst, or upon or after contacting the zeolite catalyst. The former method is preferable and has been found to provide improved yields. Suitable contact times for processes of the invention are about 0.1 to about 100 seconds, more preferably about 1 to about 20 seconds. Inert gases such as nitrogen can be used to sweep the reacted products from the reaction zone. The catalyst bed can be a fixed or moving catalyst bed (e.g. a fluid bed).

The reaction crude exiting the reaction zone can be collected, and conventional isolation techniques used to recover the products of interest. For example, reaction crudes containing 2- or 4-vinylpyridine can be fractionally distilled to recover the vinylpyridine in a purity exceeding about 95%.

For the purpose of promoting a further understanding of the invention and its principles and advantages, the following specific Examples are provided. It will be understood that these Examples are illustrative, and not limiting, of the invention.

EXAMPLES 1–9

Vapor-Phase Preparations of 2-Vinypyridine over 5% Cesium-Modified Zeolite Catalyst A number of reactions were performed in which 2-vinylpyridine was prepared by reacting formaldehyde (FM) and α-picoline over a zeolite catalyst (MFI) modified with cesium at a level of 5 weight percent. These runs are summarized in Table 1 below. The catalyst was prepared by mixing zeolite MFI (ZSM-5, PQ Corporation, silica/alumina ratio=50) with colloidal $SiO_2$ (Ludox AS-40), drying overnight at 80° C., and calcining at 550° C. for 6 hours. The material was then crushed and sieved to recover the 0.5–1.0 mm particle size range. The resulting material contained about 80% $H^+$-zeolite and 20% $SiO_2$ binder. Pellets of this bound zeolite were contacted with an aqueous solution of cesium nitrate and stirred occasionally over a 24-hour period. The water was removed at 60° C. and the resulting cesium-nitrate-loaded pellets were recovered and charged to a quartz reactor, and calncined at 500° C. for at least 4 hours to ensure decomposition of the nitrate salt to the oxide. A catalyst bed of 4.0 g (0.5–1.0 mm particle size range) was utilized, and the quartz reactor was positioned in the isothermal region of a 1.0" tube furnace. Approximately 6–8 mL of glass beads (about 4 mm diameter) were charged above the catalyst bed to serve as a feed vaporization zone. A Harvard syringe pump was used to deliver the liquid feed, via a 1/16" outer diameter Teflon transfer line, into a 316 stainless steel (SS) needle at flow rates of 2.0–8.0 mL/hour (4.0 mL/hour was typically used). The liquid feed was dripped onto the glass beads from a height of about 3 to 4 cm whereupon it was vaporized.

The runs used an α-picoline-$CH_2O$ liquid feed made from 99% grade α-picoline and 37% wt formaldehyde (MeOH<1%) mixed in the desired molar ratio (α-pic/formaldehyde=0.83).

Except for Example 9, the runs used nitrogen carrier gas to sweep the products from the reactor and the flow rate was set at about 40 mL/min. For comparison purposes, Example 9 was conducted with no gas flow. The reactor effluent was cooled to room temperature and the resulting liquid products were recovered, weighed, and analyzed by gas chromatography (GC).

Each run lasted 3 to 5 hours with samples being collected every hour in separate test periods. The reported hours-on-stream (HOS) is the end-point of each test period. At the end of each run, the catalyst was regenerated in flowing air (40 mL/min) at 550° C.

The weighed reaction crude from each test period was spiked with a known amount of 2,4-lutidine which served as an internal GC standard. The GC analyses were performed on a Shimadzu GC-14A fitted with a 50 m (0.32 mm inner diameter) FFAP capillary column and a FID (program=100° C.-9 min, 6° C./min, 200° C.-16 min, 16° C./min, 250° C.-15 min). The resulting data were normalized to account for reduced mass balances likely caused by fluctuations of the syringe pump motor or minute leaks from the syringe barrel and Luer-lock connection under pressure. The α-picoline (α-Pic) conversion, 2-vinylpyridine (2-VP) selectivity, 2ethylpyridine (2-EtP) selectively, and 2-vinylpyridine yield are reported as $\%X^{\alpha Pic}$, $\%S^{2VP}$, $\%S^{2EtP}$, and $\%Y^{2VP}$, respectively. The 2-vinylpyridine productivity is in units of g/g cat/h. The reported W/F values are based on weight of α-picoline fed per hour with units of g cat/g picoline/h.

TABLE 1

| | Run conditions | | | | 2-VP prod g/gcat/ | Results | | | | 2-VP/2-EtP |
|---|---|---|---|---|---|---|---|---|---|---|
| Ex. | αPic/ $C_1$ | W/F | HOS | T/° C. | h | $\% X^{\alpha PIC}$ | $\% S^{2VP}$ | $\% S^{2EtP}$ | $\% Y^{2VP}$ | Mole ratio |
| 1 | 0.83 | 3.96 | 5 | 400 | 0.09 | 45 | 87 | 3 | 40 | 29.0 |
| 2 | | 1.98 | 5 | 400 | 0.18 | 42 | 81 | 2 | 34 | 40.5 |
| 3 | | 0.99 | 4 | 400 | 0.24 | 28 | 80 | 2 | 23 | 40.0 |
| 4 | | 1.32 | 3 | 400 | 0.23 | 34 | 82 | 2 | 28 | 41.0 |
| 5 | | 1.98 | 4 | 350 | 0.13 | 33 | 77 | 2 | 25 | 38.5 |
| 6 | | 1.98 | 5 | 450 | 0.17 | 49 | 72 | 5 | 31 | 14.4 |
| 7 | | 1.98 | 4 | 425 | 0.19 | 41 | 84 | 4 | 34 | 21.0 |
| 8 | | 1.98 | 2 | 400 | 0.19 | 40 | 86 | 2 | 34 | 43.0 |
| 9 | | 1.98 | 3 | 400 | 0.21 | 43 | 90 | 3 | 39 | 30.0 |

These data demonstrate that 2-vinylpyridine is produced effectively, with high selectivity and yield, by the vapor-phase reaction of α-picoline and formaldehyde over a medium pore zeolite catalyst modified with cesium. In addition, 2-ethylpyridine byproduct formation was relatively low even when using a low picoline:formaldehyde molar ratio.

EXAMPLES 10–26

Preparation of 2-Vinylpyridine Using Zeolites Unmodified and Modified with Various Metal Cations Several runs were conducted in a fashion similar to Examples 1–9 above, except the metal cation used to modify the zeolite catalyst was varied, or the parent ($H^+$-form) catalyst was used. In each case employing the metal cation to introduce basic catalytic sites, effective production of 2-vinylpyridine was demonstrated, as reported in Table 2 below. The presence of Na, K, Rb, or Cs is shown to provide higher 2-vinylpyridine yields compared to the parent $H^+$-MFI.

TABLE 2

| Ex. | Catalyst | Conditions αpic/FM | W/F | HOS | T/° C. | 2-VP prod g/gcat/h | Results % $X\alpha^{PIC}$ | % $S^{2VP}$ | % $S^{2EtP}$ | % $Y^{2VP}$ | 2-VP/2-EtP Mole ratio |
|---|---|---|---|---|---|---|---|---|---|---|---|
| 10 | H-MFI (30) | 0.83 | 2.04 | 4 | 400 | 0.07 | 15 | 88 | 7 | 13 | 12.6 |
| 11 |  | 0.83 | 2.04 | 4 | 400 | 0.07 | 16 | 86 | 7 | 13 | 12.3 |
| 12 | 5% Li-MFI (50) | 0.83 | 2.04 | 4 | 400 | 0.11 | 30 | 71 | 29 | 21 | 2.4 |
| 13 | 5% Na-MFI (50) | 0.83 | 1.98 | 3 | 400 | 0.26 | 51 | 90 | 5 | 46 | 18.0 |
| 14 |  | 0.83 | 1.98 | 4 | 400 | 0.21 | 45 | 92 | 7 | 41 | 13.1 |
| 15 |  | 0.43 | 1.98 | 1, 2, 3 | 400 | 0.35 | 83 | 81 | 4 | 67 | 20.3 |
| 16 |  | 0.43 | 1.98 | 3 | 400 | 0.37 | 82 | 87 | 5 | 71 | 17.4 |
| 17 |  | 0.83 | 2.04 | 3 | 400 | 0.25 | 50 | 93 | 4 | 46 | 23.3 |
| 18 | 5% K-MFI (50) | 0.83 | 2.04 | 3 | 400 | 0.23 | 45 | 98 | 3 | 44 | 32.7 |
| 19 |  | 0.83 | 2.04 | 3 | 400 | 0.23 | 45 | 98 | 3 | 44 | 32.7 |
| 20 |  | 0.83 | 2.04 | 3 | 450 | 0.20 | 39 | 95 | 5 | 38 | 19.0 |
| 21 |  | 0.83 | 2.04 | 3 | 350 | 0.19 | 34 | 98 | 2 | 34 | 49.0 |
| 22 | 5% Rb-MFI (50) | 0.83 | 1.98 | 3 | 400 | 0.24 | 46 | 94 | 3 | 44 | 31.3 |
| 23 |  | 0.83 | 1.98 | 3 | 400 | 0.23 | 45 | 92 | 3 | 42 | 30.7 |
| 24 |  | 0.83 | 1.98 | 2 | 350 | 0.18 | 32 | 97 | 3 | 32 | 32.3 |
| 25 | 2% K-7.5% Cs- | 0.83 | 1.98 | 4 | 400 | 0.16 | 32 | 94 | 3 | 30 | 31.3 |
| 26 | MFI (50) | 0.83 | 1.98 | 4 | 400 | 0.16 | 31 | 93 | 3 | 29 | 31.0 |

EXAMPLES 27–28

Preparation of Other Vinyl-Substituted Heterocycles

The procedure of Examples 1–8 was repeated, except using γ-picoline (γPic) or 2-methylpyrazine (2MePyraz) as the nitrogenous heterocycle instead of α-picoline, to prepare the corresponding vinyl-substituted heterocycles, 4-vinylpyridine and 2-vinylpyrazine. In each case the effective production of the vinyl compound was achieved, as shown in the run summaries in Table 3.

TABLE 3

| Ex. | Conditions Het. Feed | W/F | HOS | Results % $X^{PIC}$ | % $S^{VP}$ | % $Y^{VP}$ |
|---|---|---|---|---|---|---|
| 27 | γPic | 1.98 | 3 | 56 | 79 | 44 |
| 28 | 2MePyraz | 1.98 | 4 | 33 | 100 | 33 |

EXAMPLES 29–33

Preparation of Vinyl-Substituted Heterocycles Using Various C1 Feeds

The procedure of Examples 1–8 was repeated, except using various $C_1$ feeds including 37% aqueous formaldehyde, 52% aqueous formaldehyde (FM) and trioxane (Trx, treated as 3 equivalents of formaldehyde). The results are set forth in Table 4, and demonstrate that the $C_1$ feed can be varied while nonetheless achieving an effective preparation of the vinyl compound. Further, the use of higher concentrated feeds of formaldehyde, and of trioxane, proved advantageous in the synthesis.

TABLE 4

| Ex. | Conditions $C_1$ | αPic/$C_1$ | W/F | HOS | 2-VP prod g/gcat/h | Results % $X\alpha^{PIC}$ | % $S^{2VP}$ | % $S^{2EtP}$ | % $Y^{2VP}$ | 2-VP/2-EtP Ratio |
|---|---|---|---|---|---|---|---|---|---|---|
| 29 | 37% FM | 0.83 | 1.98 | 5 | 0.18 | 42 | 81 | 2 | 34 | 40.5 |
| 30 | 37% FM | 0.83 | 1.98 | 2 | 0.19 | 40 | 86 | 2 | 34 | 43.0 |
| 31 | 52% FM | 0.83 | 1.57 | 3 | 0.26 | 46 | 83 | 3 | 39 | 27.7 |
| 32 | Trx | 0.97 | 2.56 | 4 | 0.18 | 53 | 95 | 5 | 50 | 19.0 |
| 33 | Trx | 0.65 | 2.88 | 4 | 0.20 | 64 | 95 | 6 | 61 | 15.8 |

EXAMPLES 34–54

Preparation of 2-Vinylpyridine Using Various Metal-Loaded Zeolite Catalysts

In a series of runs, 2-vinylpyridine was prepared using the general method of Examples 1–8, except varying the catalyst. The results, summarized in Table 5 below, demonstrate that varied metals can be used to modify the zeolite to substantially improve vinylpyridine production relative to the parent zeolite. In the Table, the $SiO_2/Al_2O_3$ ratio for a given catalyst is set forth in parenthesis after the catalyst designation, where appropriate.

TABLE 5

| Ex. | Catalyst | Conditions | | | | 2-VP prod | Results | | | | 2-VP/2-EtP |
|-----|----------|------------|---|---|---|-----------|---------|---|---|---|------------|
|     |          | αPic/FM | W/F | HOS | T/° C. | g/gcat/h | % Xα$^{PIC}$ | % S$^{2VP}$ | % S$^{2EtP}$ | % Y$^{2VP}$ | Mole ratio |
| 34 | 0.47% Mg-MFI (50) | 0.83 | 2.04 | 3 | 400 | 0.06 | 15 | 82 | 13 | 12 | 6.3 |
| 35 |  |  |  | 3 | 400 | 0.06 | 14 | 82 | 12 | 12 | 6.8 |
| 36 | 0.84% Ca-MFI (50) | 0.83 | 1.98 | 4 | 400 | 0.10 | 23 | 83 | 9 | 19 | 9.2 |
| 37 |  |  |  | 4 | 400 | 0.10 | 21 | 89 | 9 | 19 | 9.9 |
| 38 | 0.96% Sc-MFI (50) | 0.83 | 2.04 | 3 | 400 | 0.03 | 11 | 68 | 14 | 7 | 4.9 |
| 39 |  |  |  | 3 | 350 | 0.02 | 9 | 58 | 8 | 5 | 7.3 |
| 40 | 1.3% Ga-MFI (50) | 0.83 | 2.04 | 3 | 400 | 0.07 | 21 | 63 | 6 | 13 | 10.5 |
| 41 |  |  |  | 3 | 400 | 0.06 | 21 | 63 | 5 | 12 | 12.6 |
| 42 | 3.7% Tl-MFI (50) | 0.83 | 2.04 | 3 | 400 | 0.18 | 41 | 86 | 6 | 35 | 14.3 |
| 43 |  |  |  | 3 | 400 | 0.17 | 41 | 83 | 6 | 34 | 13.8 |
| 44 | 3.7% Tl-Silicalite | 0.83 | 1.98 | 4 | 400 | 0.07 | 19 | 59 | 10 | 11 | 5.9 |
| 45 |  |  |  | 4 | 400 | 0.04 | 10 | 73 | 8 | 7 | 9.1 |
| 46 | Cu-MFI (30) | 0.83 | 1.98 | 3 | 400 | 0.07 | 25 | 57 | 6 | 14 | 9.5 |
| 47 |  |  |  | 3 | 400 | 0.08 | 25 | 64 | 5 | 16 | 12.8 |
| 48 | 3% Ag-MFI (50) | 0.83 | 2.04 | 4 | 400 | 0.07 | 23 | 65 | 19 | 15 | 3.4 |
| 49 |  |  |  | 4 | 400 | 0.07 | 20 | 71 | 20 | 13 | 3.6 |
| 50 | 10% Zn-MFI (50) | 0.83 | 2.04 | 3 | 400 | 0.01 | 7 | 46 | 39 | 3 | 1.2 |
| 51 | 5% Sn-MFI (150) | 0.83 | 2.04 | 3 | 400 | 0.04 | 13 | 81 | 12 | 9 | 6.8 |
| 52 |  |  |  | 3 | 450 | 0.04 | 10 | 76 | 23 | 8 | 3.3 |
| 53 | 3% Pb-MFI (50) | 0.83 | 1.98 | 3 | 400 | 0.07 | 23 | 59 | 21 | 14 | 2.8 |
| 54 |  |  |  | 4 | 400 | 0.07 | 16 | 85 | 24 | 14 | 3.5 |

While the invention has been illustrated and described in detail in the foregoing description, the same is to be considered as illustrative and not restrictive in character, it being understood that only the preferred embodiment has been shown and described and that all changes and modifications that come within the spirit of the invention are desired to be protected.

All publications cited herein are indicative of the level of skill in the art and are hereby incorporated by reference as if each had been individually incorporated by reference and fully set forth.

What is claimed is:

1. A process for preparing a vinylpyridine, comprising:

reacting a α-picoline or γ-picoline with formaldehyde in vapor phase in the presence of a zeolite catalyst, said catalyst modified with at least one metal cation, so as to form a corresponding 2-vinylpyridine or 4-vinylpyridine compound.

2. The process of claim 1, wherein the metal cation is an alkali metal cation.

3. The process of claim 2, wherein the metal cation is selected from the group consisting of sodium, potassium, rubidium, cesium, and thallium cations.

4. The process of claim 1, wherein said reacting is at a temperature of about 250° C. to about 500° C.

5. The process of claim 1, wherein said zeolite catalyst has a constraint index of about 0.5 to about 12.

6. The process of claim 5, wherein said zeolite catalyst is MFI or MEL.

7. The process of claim 1, which comprises reacting α-picoline with formaldehyde to form 2-vinylpyridine.

8. The process of claim 1, which comprises reacting γ-picoline with formaldehyde to form 4-vinylpyridine.

9. The process of claim 1, and also comprising the step of isolating said 2-vinylpyridine or 4-vinylpyridine compound.

10. The process of claim 1, which comprises reacting formaldehyde with α-picoline in a molar ratio less than about 3:1, respectively, to form 2-vinylpyridine.

11. The process of claim 1, which comprises reacting formaldehyde with γ-picoline in a molar ratio less than about 3:1, respectively, to form 4-vinylpyridine.

12. The process of claim 1, wherein said catalyst is comprised about 1% to about 10% by weight of said metal cation.

13. A process for preparing an alkenyl-substituted nitrogenous heterocycle, comprising:

reacting an alkyl-substituted nitrogenous heterocycle with formaldehyde in vapor phase in the presence of a zeolite catalyst modified with at least one metal cation, so as to form a corresponding alkenyl-substituted nitrogenous heterocycle.

14. The process of claim 13, wherein said alkyl-substituted nitrogenous heterocycle is α-picoline.

15. The process of claim 13, wherein said alkyl-substituted nitrogenous heterocycle is γ-picoline.

16. The process of claim 13, wherein said alkyl-substituted nitrogenous heterocycle is 2-methylpyrazine.

17. The process of claim 13, wherein said alkyl-substituted nitrogenous heterocycle is 4-ethylpyridine.

18. The process of claim 13, wherein said alkyl-substituted nitrogenous heterocycle is 2-ethyl-3,5-dimethylpyridine.

19. The process of claim 13, wherein said zeolite catalyst has a constraint index in the range of about 0.5 to about 12.

20. The process of claim 19, which comprises reacting said methyl-substituted nitrogenous heterocycle with formaldehyde in a molar ratio less than about 3:1, respectively.

21. The process of claim 20, wherein said metal cation is selected from the group consisting of sodium, potassium, rubidium, cesium, and thallium cations.

22. The process of claim 21, wherein said metal cation is a sodium cation.

* * * * *